(12) United States Patent
Downie et al.

(10) Patent No.: US 8,998,261 B2
(45) Date of Patent: Apr. 7, 2015

(54) MOUNTING STRUCTURE

(75) Inventors: Andrew Downie, Cheshire (GB); Alexander James Redman, Surrey (GB)

(73) Assignee: Bentley Motors Limited (GB)

( * ) Notice: Subject to any disclaimer, the term of this patent is extended or adjusted under 35 U.S.C. 154(b) by 16 days.

(21) Appl. No.: 13/985,423

(22) PCT Filed: Feb. 17, 2012

(86) PCT No.: PCT/GB2012/050360
§ 371 (c)(1),
(2), (4) Date: Aug. 14, 2013

(87) PCT Pub. No.: WO2012/110827
PCT Pub. Date: Aug. 23, 2012

(65) Prior Publication Data
US 2014/0154039 A1    Jun. 5, 2014

(30) Foreign Application Priority Data
Feb. 17, 2011   (GB) .................................. 1102743.0

(51) Int. Cl.
*B60R 22/03*   (2006.01)
*B25J 18/00*   (2006.01)
(Continued)

(52) U.S. Cl.
CPC ................ *B25J 18/00* (2013.01); *B60R 22/03* (2013.01); *B60R 2022/021* (2013.01); *A61B 19/22* (2013.01); *A61B 19/2203* (2013.01); *A61B 17/00* (2013.01); *A61M 5/00* (2013.01)

(58) Field of Classification Search
CPC .......................... B60R 2022/021; B60R 22/03
USPC ...................... 280/805, 801.2; 297/481, 473
See application file for complete search history.

(56) References Cited

U.S. PATENT DOCUMENTS 4,989,901 A * 2/1991 Adomeit .................... 280/801.2
5,791,687 A * 8/1998 Gotou et al. .................. 280/805
(Continued)

FOREIGN PATENT DOCUMENTS

| DE | 195 28 715 A1 | 2/1997 |
| DE | 196 51 092 A1 | 7/1997 |

(Continued)

OTHER PUBLICATIONS

Wolfgang Kasubke, Belt i.e. three-point seat belt of cabriolet vehicle, guiding device, has belt vibration sensor provided for detecting belt vibrations e.g. flutter of seat belt, and for generating belt vibration signal relative to belt vibrations, May 8, 2008, EPO, DE 10 2006 052 088 A1, Machine Translation of Description.*

*Primary Examiner* — James English
(74) *Attorney, Agent, or Firm* — Salter & Michaelson

(57) ABSTRACT

A mounting structure for mounting a support for a seat belt to a vehicle, arranged so that when mounted to a vehicle it will move relative to the vehicle in a first range of directions under application of a first force urging the mounting structure in one of the range of directions, but will not move relative to the vehicle in a direction outside the first range of directions when a second, greater, force is applied urging the mounting structure in such a direction. The structure may have a bracket (7) secured to a vehicle by bolts (18) passing through slots (15) in the bracket, allowing the bracket to move generally in the direction of the slots, but not otherwise. De-couplers, in which toothed flanges (20) on collars (19) through which the bolts extend bear against raised pads on u-shaped washer structures (23) may be disposed between the bolt heads and the bracket to limit the force applied to the bracket and enable the applied force at which the bracket will move relative to the vehicle to be controlled.

13 Claims, 5 Drawing Sheets

(51) Int. Cl.
*A61B 19/00* (2006.01)
*A61B 17/00* (2006.01)
*A61M 5/00* (2006.01)
*B60R 22/02* (2006.01)

(56) References Cited

U.S. PATENT DOCUMENTS 6,250,681 B1   6/2001   Takahashi et al.
7,686,338 B2 *   3/2010   Dallwig et al. ............ 280/801.1
2013/0313814 A1 *   11/2013   Marziani ....................... 280/805

FOREIGN PATENT DOCUMENTS

DE       100 53 673 A1       5/2002
DE       102006052088    *   5/2008
EP       0 359 954            3/1990
EP       1 854 706 A1        11/2007

* cited by examiner

MOUNTING STRUCTURE

TECHNICAL FIELD OF THE INVENTION

The present invention relates to a mounting structure for mounting a support for a seat belt to a vehicle. It also relates to a de-coupler assembly for use in the mounting structure, and for other applications.

BACKGROUND TO THE INVENTION

To serve their purpose and meet regulatory requirements vehicle seat belts must be securely mounted to the vehicle. Motor cars are usually provided with three point seat belts which have an upper mounting point from which a shoulder strap is supported. In an open top motor car the upper mounting point for the front seat belts is typically on the rear quarter panel of the vehicle. For larger vehicles, and vehicles with doors intended to allow access for rear seat occupants, the upper mounting point for the seat belts can be spaced some distance behind the front seats and thus difficult for front seat occupants to reach. This problem is often addressed by provision of a seat belt presenter comprising a motor driven arm mounted in the rear quarter panel which extends from the rear quarter panel to offer the seat belt to a front seat occupant.

The upper part of the outer surface of a rear quarter panel, to the inside of a vehicle, presents a potential head impact area for rear seat passengers of the vehicle in the event of very rapid deceleration of the vehicle, such as in a collision. To lessen the risk of serious head injury and again to meet regulatory requirements certain potential head impact areas of a vehicle must be able to absorb impact and thus limit the magnitude of deceleration of a head which contacts the surface in a collision situation. One way to lessen the effects of impact with the upper part of a rear quarter panel is to provide a casing which forms the outer surface of the panel which is spaced from the underlying structure of the panel. Deformation of the casing can then absorb the energy of an impact before a passenger comes into contact with the less yielding underlying structure. A problem with this, though, is that spacing the casing from the underlying structure necessarily reduces space inside the vehicle. This is a particular problem with open top vehicles where the rear quarter panel is often bulkier than for closed vehicles owing to the extra structure required to compensate for the lack of a fixed roof and or to provide storage. And it is especially a problem where the rear quarter panel is required to house a seat belt presenter which must necessarily be mounted towards the top of the panel.

Embodiments of the present invention have been made in consideration of these problems.

SUMMARY OF THE INVENTION

According to an aspect of the present invention there is provided a mounting structure for mounting a support for a seat belt to a vehicle, the mounting structure being arranged so that when mounted to a vehicle it will move relative to the vehicle in a first range of directions under application of a first force urging the mounting structure in one of the range of directions, but will not move relative to the vehicle in a direction outside the first range of directions when a second, greater, force is applied urging the mounting structure in such a direction, the mounting structure comprising a bracket having one or more elongate slots extending therethrough, through which a fastener may extend to fasten the bracket to a vehicle.

The mounting structure enables a seat belt mounting to be provided which provides the necessary support for a seat belt, by resisting loads applied by the seatbelt, but which can be arranged to yield to, and thus absorb, forces applied in different directions, such as the result of a head impact.

The mounting structure may be arranged so that it will not move relative to the vehicle in a second range of directions which is a subset of the range of directions which is outside the first range of directions. The first and second ranges of directions may be generally perpendicular to each other. When mounted in a vehicle the mounting structure may be arranged to be movable relative to the vehicle in a sideways direction, but not in a forwards direction and thus be able to absorb a sideways head impact, but resist the load applied to a seatbelt by a front seat occupant during a collision.

A fastener may extend through the or each slot in the bracket to fasten the bracket to a vehicle. The fastener may be sized to be able to move along the length of the slot and could be a bolt, stud, pin or other suitable fastener.

In use, each fastener may extend through a respective collar, the collar having a flange extending from one end thereof. In one embodiment the flange extends around one end of the collar. Teeth may be formed on a surface of the flange.

Each fastener may extend through a respective washer structure positioned adjacent to the flange of the collar so that when the fastener is used to fasten the bracket to a vehicle the flange of the collar is urged into contact with the washer structure. The washer structure may define an open ended slot. The washer structure may comprise two substantially parallel sidewalls arranged to capture the flange of the collar in order to retain the collar relative to the washer.

The bracket may be mounted to the vehicle with fasteners associated with a de-coupler assembly as discussed below.

The mounting structure may comprise a second bracket. The second bracket may be arranged to be mounted to a vehicle so that it is fixed relative to the vehicle. The second bracket may comprise a stop arranged to limit relative movement between the two brackets in one or more directions.

A support for a seat belt may be mounted to the first bracket. The stop of the second bracket may be arranged to limit movement of the support for a seat belt. The support for a seatbelt may be a loop.

A seatbelt presenter mechanism may also be mounted to the bracket.

The mounting structure may be mounted to a vehicle, such as a motor car.

The mounting structure may be mounted to a rear quarter panel of a motor car.

The mounting structure may be arranged to support an upper mounting point of a three point seat belt for a front seat occupant of the motor car, According to another aspect of the present invention there is provide a vehicle comprising a mounting structure for mounting a support for a seatbelt to the vehicle, the mounting structure being arranged so that it will move relative to the vehicle in a first range of directions under application of a first force urging the mounting structure in one of the range of directions, but will not move relative to the vehicle in a direction outside the first range of directions when a second, greater, force is applied urging the mounting structure in such a direction, wherein the mounting structure comprises a bracket mounted to the vehicle by way of a fastener which extends through an elongate slot formed in either the vehicle and/or the bracket.

It will be appreciated that the invention can be effected by providing a slot in the vehicle rather than in the bracket of the mounting structure.

According to another aspect of the present invention there is provided a de-coupler assembly for use with a fastener intended to pass through an aperture in one component and urge it towards another component to fasten the components together but permit relative sliding movement of the two components when a predetermined force is applied, the assembly comprising a spacer having a first portion intended to pass through the aperture in the first component and contact the second component and a second portion intended to overlie the first component, and a washer structure intended to be disposed between the second portion of the spacer and the first component.

Such a de-coupler is useful where one component is bolted to another with the bolt passing through a slot in the first component which allows the first component to slide relative to the second component. Movement of the spacer towards the first component is limited by its contact with the second component. Thus the force applied to the first component urging it into contact with the second component is limited by the dimensions of the first component and the washer structure and consequently the force required to slide the two components relative to one another is also limited.

The spacer may comprise a collar with flange extending therefrom at one end. The collar should be chosen to have a size that will allow it to pass through an aperture in the first component, and the flange to have a size that will not pass through an aperture in the first component. A fastener such as a bolt, stud or pin may pass though the collar.

Thus, the depth of the collar and the thickness of the washer structure can be selected to determine the force the fastener can apply to urge the first component to the second component and hence the force required to slide the first component relative to the second component.

Teeth may be formed on a surface of the flange intended, in use, to face the washer structure. Raised pads may be formed on the surface of the washer structure intended to contact the teeth on the flange. By varying the number and depth of the teeth, and material of the washer structure the force required to slide the first and second components relative to one another can be tuned.

The washer structure may define an open ended slot. The washer structure may comprise two substantially parallel sidewalls arranged to capture the flange of the collar in order to retain the collar relative to the washer. Slots may be formed in the sidewalls into which edges of the flange may extend. Facing surfaces of the sidewalls may be stepped and the flange may be captured beneath the steps.

The collar and flange may be formed in a single piece from metal, for example steel.

The washer structure may be formed from a resilient material. The washer structure may be formed from a from a plastics material. A glass reinforced material may be used such as PP GF30.

DETAILED DESCRIPTION OF THE DRAWINGS

In order that the invention may be more clearly understood an embodiment thereof will now be described, by way of example only, with reference to the accompanying drawings, of which:

DETAILED DESCRIPTION

Figure 1:
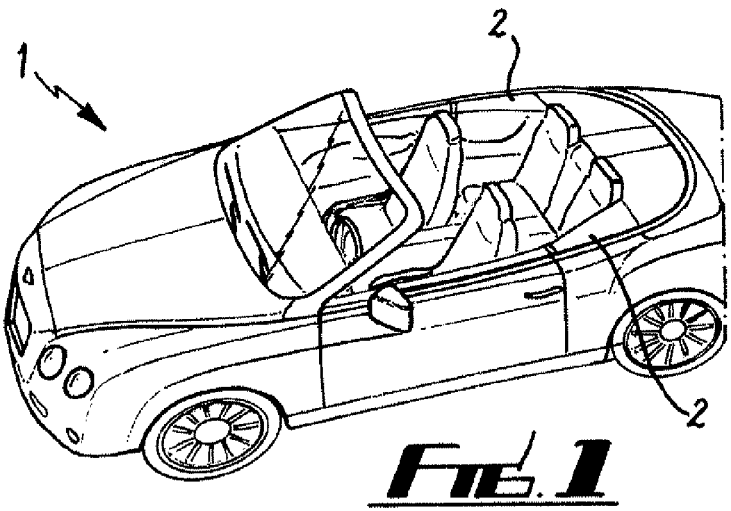
FIG. 1 is a perspective view from above of a two door open top motor car.

In the following, like reference numerals are used to refer to like features throughout. The terms up, down, top and bottom, are used to describe the illustrated apparatus in the orientation shown in the drawings, but should not be taken as otherwise limiting.

Referring to the drawings a two door open top motor car 1 comprises rear quarter panels 2. Each rear quarter panel houses an inertia reel seat belt (not shown) for the corresponding front seat of the vehicle. The seat belt pays out through a slot 3 formed in a forward facing surface of the internal (to the vehicle) casing of the rear quarter panel.

Figure 2:
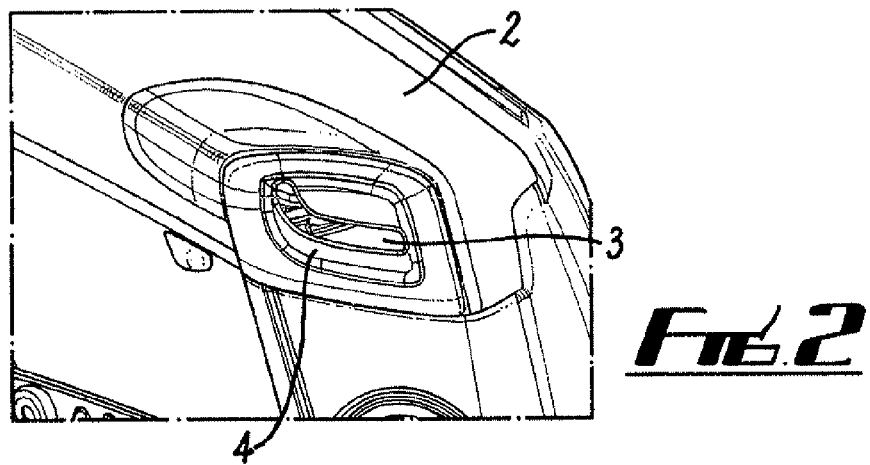
FIG. 2 is an enlarged perspective view of an inside rear quarter panel of the motor car of FIG. 1.
Figure 3:
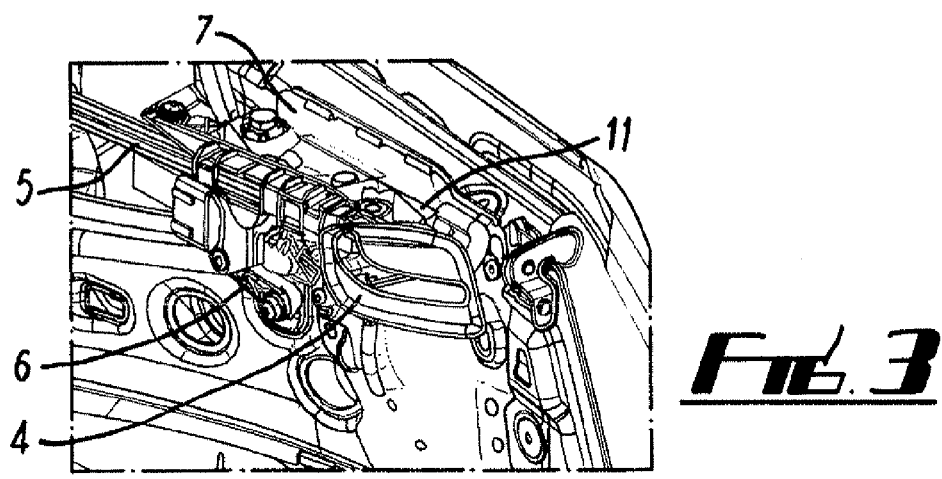
FIG. 3 is a perspective view of the rear quarter panel of FIG. 2 with outer casing removed to reveal a seat belt mounting.

Owing to the length of the vehicle and the size of its doors, which must allow sufficient space for entry and exit of rear seat passengers, the forward facing surface of the rear quarter panels, in which the slot 3 is formed, is positioned somewhat behind the corresponding front seat. This makes it difficult for a front seat occupant to reach the seat belt in order to put it on. To overcome this problem a seat belt presenter mechanism is provided. The slot 3 through which the seat belt pays out is formed in a panel 4 mounted on an elongate arm 5. The arm 5 may be extended from and retracted into the casing of the rear quarter panel in order to move the panel 4 though which the seatbelt extends towards a front seat passenger to enable them to reach the seat belt comfortably, and then return it to the position shown in FIG. 2. The arm is driven by a drive mechanism. The operation of seat belt presenters is known, and so will not be described in further detail.

The seat belt presenter arm 5 is slidably mounted in a guide 6 which is, in turn, mounted above and to the side of a bracket 7 mounted to the rear quarter panel. The seat belt presenter arm 5 and panel 4, is solely provided to facilitate use of the seat belt and does not serve to support load applied to the seatbelt by a passenger under vehicle impact conditions. Rather, a load bearing upper mounting point for the seat belt is provided by a metal D-loop 8 through which the seat belt extends, and which is also mounted to the bracket 7.

Figure 5:
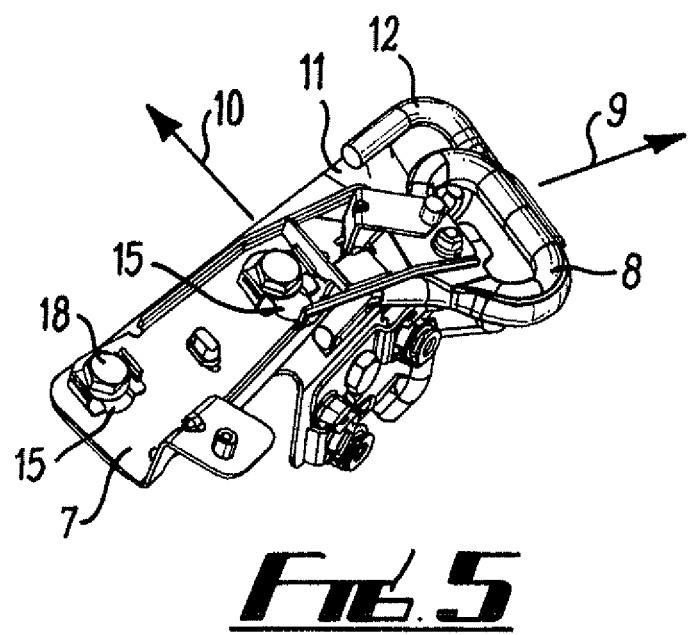
FIG. 5 is a corresponding view to FIG. 4 but with the seat belt presenter arm removed.

In order that the seat belt can fulfil its function, and meet regulatory requirements, the D-loop must be able to bear significant loads applied in the general direction of arrow 9 of FIG. 5. This load must be borne, in turn, by the bracket 7.

However there is also a conflicting consideration. For the safety of rear seat passengers in a vehicle impact situation, and also to meet regulatory requirements, there is a need to limit the acceleration of a rear seat passenger's head in the event of impact with the inside of an upper part of the rear quarter panel, specifically the area surrounding the seat belt and presenter mounting. The casing of the rear quarter panel on the inside of the vehicle will be initial point of contact of a passenger in an impact scenario and can be designed to deform to reduce acceleration in head impact. However, for the casing itself to provide the necessary protection would necessitate it being spaced well away from underlying non-yielding structure, increasing intrusion of the rear quarter panel into the interior of the vehicle and thus reducing passenger space. This is a particular problem with an open top vehicle where the rear quarter panel structure is often bulkier than for a corresponding closed body owing to the need to increase the stiffness of the bodywork to compensate for the lack of a roof, and to provide space in which to store a hood or folding roof.

So, if the amount of space between the inside casing of the rear quarter panel and the underlying structure (in this case the seat belt presenter arm 5, its mounting 6 and the D-loop 8, all mounted to bracket 7) is to be minimised the underlying structure must be capable of yielding to a moderate force so as to reduce acceleration in a head impact. With the illustrated arrangement this requires that bracket 7 is able to move in response to moderate force applied generally in the direction of arrow 10 in FIG. 5.

In the illustrated arrangement the conflicting requirements of the bracket's reaction to force are met by mounting the bracket 7 to underlying structure in such a way that the bracket will move relative to that structure in the general direction of arrow 10, but not in other direction, under application of a moderate force and by provision of a secondary load bearing structure to arrest movement of the D-Loop in the event that it moves in the direction of arrow 9. Both provisions are discussed in further detail below. In addition the raised parts of bracket 7, to which the seat belt presenter arm 5 is mounted are designed to deform under a head impact situation.

The bracket 7 (now referred to as the upper bracket) is mounted over a lower bracket 11, and both brackets are mounted to the underlying structure of the vehicle, known as the body in white. Mounted to the lower bracket 11 is a curved metal bar 12, forming a stop, which extends around the front end of the rear quarter panel at a level coinciding with a lip 13 formed on the underside of the D-loop 8. The lip 13 is shaped to accommodate the bar 12 and contact between the D-loop 8 and the bar 12 will prevent relative movement between the two. The bar 12 therefore provides a limit to displacement of the D-loop as a result of relative movement of the upper and lower brackets in a number of directions.

The two brackets 7 and 11 are bolted to the body in white. Front and rear substantially circular apertures 14 are formed in the lower bracket 11, and corresponding elongate straight, parallel sided, slots 15 are formed in the upper bracket 7. A de-coupler 16 is placed in each slot and a respective bolt 18 extends through each de-coupler, slot, aperture in the lower bracket, a corresponding aperture in the body in white and into a captive nut 17. The apertures in the lower bracket 11 and body in white closely accommodate the bolts so that the lower bracket 11, and hence also the bar 12, are fixed relative to the body in white. The slots 15 in the upper bracket allow movement of the upper bracket 7 relative to the lower bracket 11, and body in white, generally along the direction of arrow 10 although there is sufficient clearance in the slots to allow the upper bracket to move so that it slides relative to the lower bracket at one bolt and pivots about the other.

The force required to move the upper bracket 7 relative to the lower bracket 11 depends on friction between the two brackets and with the bolts 18, and so depends on the tightness of the bolts urging the two brackets together. It is desirable that the force at which the upper bracket 7 will move relative to the lower bracket is predictable and controllable. This is the purpose of the de-couplers.

Each de-coupler comprises a washer structure which captures a collar structure. The collar structure comprises a substantially cylindrical metal collar 19 surrounded at one end by a generally annular flange 20 which extends at two opposite points to form opposed tabs 21. On the surface of each tab directed towards the collar there are formed a series of teeth 22. The washer structure comprises washer 23 formed from a glass reinforced plastics material, such as PP GF30. The washer comprises a generally U-shaped plate 24 bounded on opposite substantially parallel outside edges by upstanding sidewalls 25. The sidewalls are thicker towards their free ends and thinner towards the plate 24. The thickness of the sidewalls changes in a single step approximately mid way along the sidewalls. An elongate slot running substantially parallel to the surface of the plate is formed towards the free edge of each side wall. A raised area 26 is formed on the surface of the plate adjacent each sidewall 25. To the underside of the plate 23, that is the side opposite to that on which the raised portions 26 are formed, sidewalls 27, significantly shorter than the sidewalls 23 on the other side, extend along opposite internal edges of the U-shaped slot formed by the plate 24. Approximately semicircular formations 28 are formed about midway along each of these sidewalls.

Figure 9:
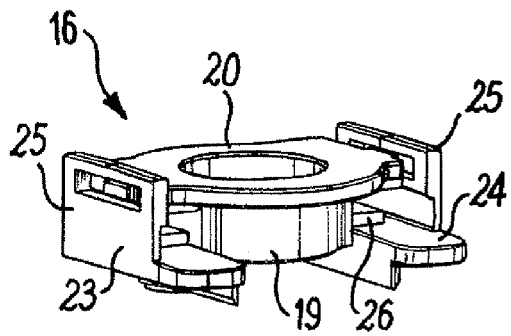
FIG. 9 is a perspective view of a de-coupler of the assembly shown in FIGS. 4 to 7 in a pre-deployed state.
Figure 10:
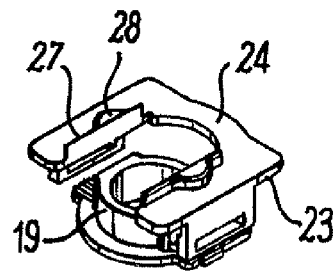
FIG. 10 is a perspective view, from the underside, of the de-coupler of FIG. 9.
Figure 11:
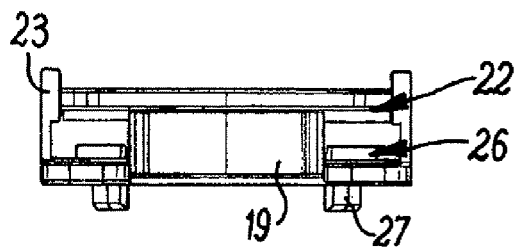
FIG. 11 is a side view of the de-coupler of FIG. 9.
Figure 12:
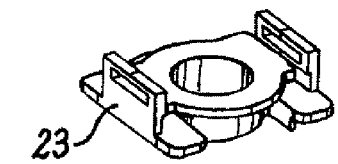
FIG. 12 is a perspective view of the de-coupler of FIG. 9 in a deployed state.
Figure 13:
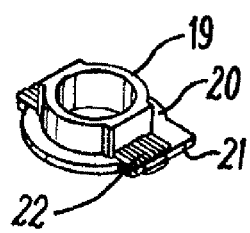
FIG. 13 is a perspective view, from below, of the collar of the de-coupler of FIG. 9.
Figure 14:
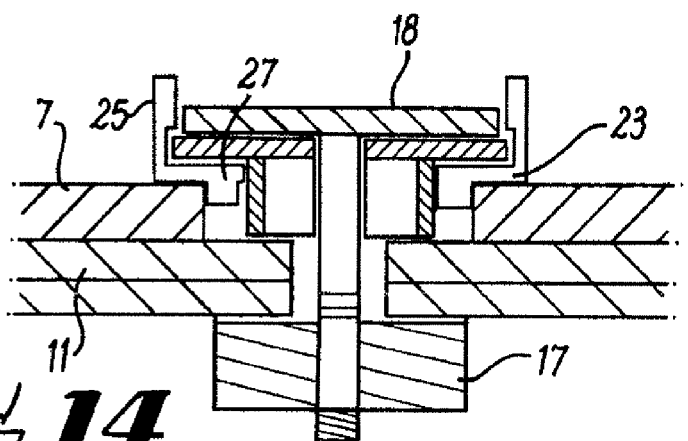
FIG. 14 is a side, cross-sectional view of the de-coupler of FIG. 9 installed in the assembly shown in FIGS. 4 to 7.

The de-couplers 16 are initially assembled as shown in FIG. 9, with the tabs 21 of the collar structure extending through the slots in the sidewalls 23. This positions the teeth 22 on the flange of the collar structure over, and spaced from, the raised portions of the washer structure. Resilient flexibility of the material of the washer structure enables the tabs of the collar structure to be inserted into the slots in its sidewalls 25.

In this state a de-coupler is placed washer structure side down into one end of a slot 15 in the upper bracket 7 with the sidewalls 27 lying adjacent the parallel edges of the slot and the open end of the U-shaped washer being directed to the other end of the slot. The sidewalls 27 extend over substantially all of the straight parallel sides of the slots 15 and shaped cut outs are formed in the sides of each slot 15 to receive the semicircular formations 28. This serves to restrict movement of the washer structures longitudinally within the slots. A bolt 18 is then passed through the collar, upper and lower brackets 7, 11, body in white and into the captive nut 17. The bolt is then tightened to a predetermined torque. This urges the collar portion of the de-coupler towards the nut 17. Initially, owing to the resilience of the washer structure, the tabs 21 of the collar structure are forced out of the slots in the sidewalls 25 and, as the collar structure moves towards the washer they then engage below the steps in the sidewalls and the teeth of the collar structure begin to bite into the raised portions 26 on the washer plate 24 and the washer is urged into contact with the surface of the upper bracket 7. The outside diameter of the collar 19 is less than the width of the slot in the upper bracket 7 and the inside diameter of the collar 19 is greater than that of the aperture through the lower bracket 11. So as the collar structure is drawn towards the nut it will contact the lower bracket. Further tightening of the bolt will now serve to increase the force urging the lower bracket against the body in white, but not the force with which the upper bracket is urged towards the lower bracket. This is determined by the relative thicknesses of the upper bracket and washer plate, the depth of the collar structure and the size and configuration of the teeth and material of the washer structure. So the force with which the upper bracket is urged against the lower bracket can be chosen through the design of the de-coupler. In turn, this affects the force required to move the upper bracket relative to the lower bracket, and this is also controlled by characteristics of the teeth and the material of the washer since relative sliding movement of the two brackets will cause the teeth to be moved relative to the washer, as discussed further below.

Figure 4:
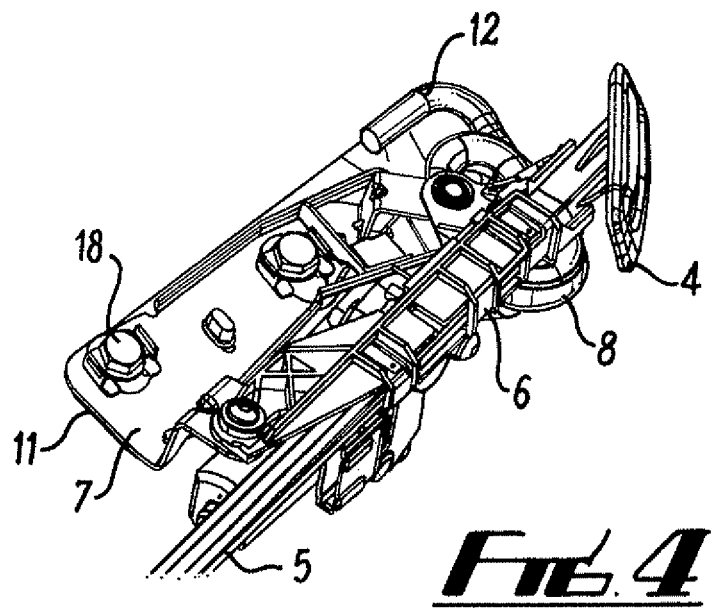
FIG. 4 is a perspective view of the seat belt mounting of FIG. 3 showing the mounting in a normal position.

In initial assembly the lower and upper brackets are mounted to the body in white. The slots 15 in the upper bracket, accommodating the de-couplers, enable the position of the upper bracket to be precisely controlled relative to the body in white and thus enable the D-loop to be accurately positioned, allowing for tolerances in the body in white. The upper bracket will thus be placed in a position substantially as shown in FIGS. 4 and 5 with the bracket at or near to the innermost position (i.e. towards the inside of the vehicle) allowed by the slots 15. In this position the D-loop is correctly positioned relative to a front seat occupant, and the seat belt presenter arm and can offer the seat belt into easy reach of the occupant. The bolts are then tightened to secure the brackets in place.

Figure 6:
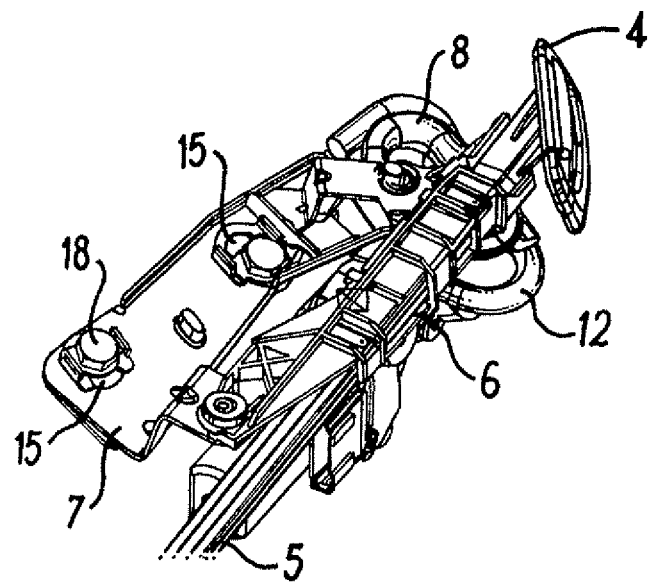
FIG. 6 is a corresponding view to FIG. 4 with the seat belt mounting in a displaced position.
Figure 7:
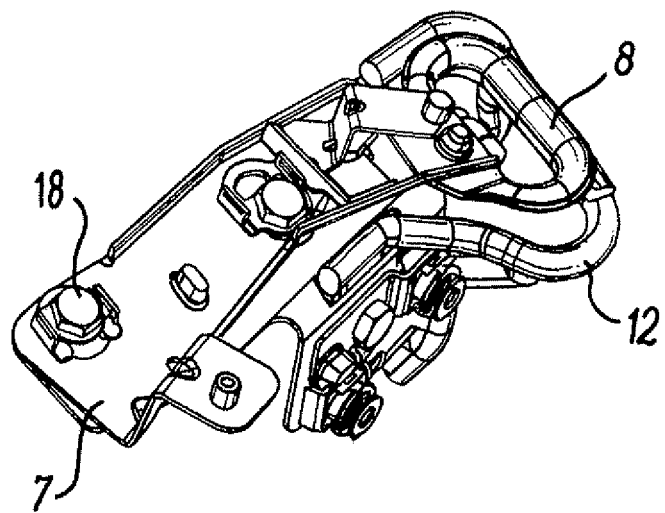
FIG. 7 is a corresponding view to FIG. 5 with the seat belt mounting guide in a displaced position.
Figure 8:
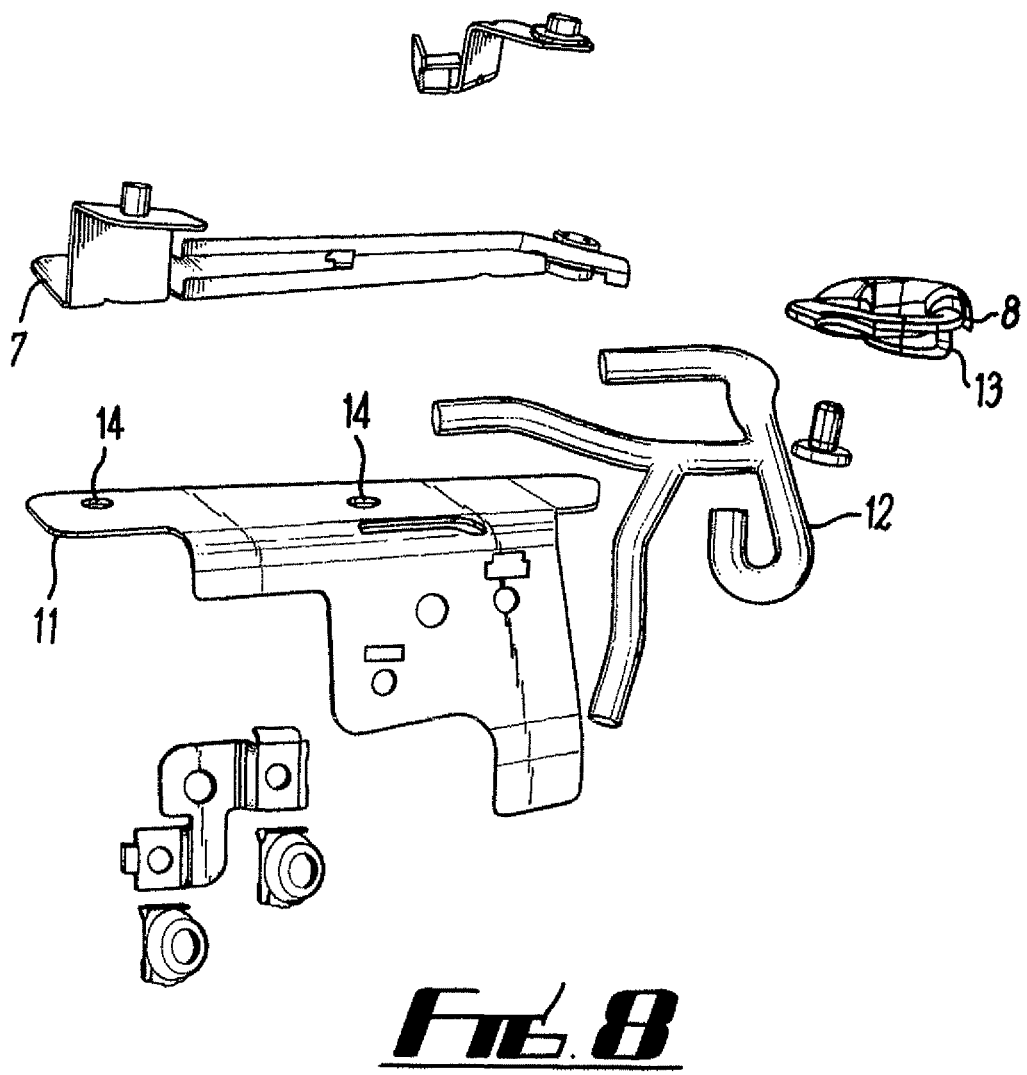
FIG. 8 is an exploded view of part of the internal structure of the rear quarter panel and seat belt mounting of FIG. 3.

In the event of a collision or other sudden deceleration of the vehicle resulting in a rear seat passenger striking the inside of the rear quarter panel in the region of the brackets and seat belt presenter initial impact of the passenger will be absorbed by the casing of the rear quarter panel until it contacts the seat belt presenter and bracket structure. Force or a component of force resulting from the impact above a chosen threshold in the direction of arrow 10 will cause the upper bracket to slide relative to the lower bracket in the direction of slots 15. Since formations 27 on the underside of the washers are engaged with the slots, the washers will tend to move with the bracket and relative to the collar structures 20 of the de-couplers, dragging the teeth of the de-couplers through the raised portions of the washers. The upper bracket may move into the position shown in FIGS. 6 and 7. In this position it will be seen that the bracket has moved so that the front bolt 18 and collar structure is now disposed at the opposite end of the slot 15 to that at which it was disposed originally. The position of the rear bolt and collar structure has remained substantially constant relative to its slot, the bracket having largely rotated about the rear bolt and collar assembly. This movement of the upper bracket enables the force of rear passenger impact on the upper part of the rear quarter panel to be absorbed and therefore limits deceleration of the rear seat passenger and so the risk of injury.

At the same time, as the vehicle decelerates, any front seat occupant wearing a seat belt passing through the D-loop will be decelerated by the seatbelt and therefore apply a significant force to the D-loop via the seat belt generally in the direction of the arrow 9. This direction is generally perpendicular to the direction of the slots 15 in the upper bracket and so the upper bracket will tend not to be displaced in this direction. In the event of any displacement, however, the lower lip 12 of the D-loop 8 will contact the curved bar 8 which will arrest further relative movement between the upper and lower brackets.

The described arrangement allows for accurate positioning of a seat belt D-loop. It also provides a D-loop which is able to properly perform its function in supporting force applied to a seatbelt, whilst allowing the seatbelt presenter and associated bracket to be displaced in an outward direction on application of a lesser force than that to be supported by the D-loop so as to limit the effects of impact of a passenger on the rear quarter panel.

The above embodiment is described by way of example only. Many variations are possible without departing from the scope of the invention as defined in the appended claims.

What is claimed is:

1. A mounting structure for mounting a support for a seat belt to a vehicle, the mounting structure being arranged so that when mounted to the vehicle the mounting structure will move relative to the vehicle in a first range of directions under application of a first force urging the mounting structure in one of the range of directions, but will not move relative to the vehicle in a direction outside the first range of directions when a second, greater, force is applied urging the mounting structure in such a direction, the mounting structure comprising a first bracket with an elongate slot extending therethrough, a decoupler assembly and a fastener extending through the decoupler assembly and the elongate slot, the fastener and decoupler assembly intended, in use, to fasten the first bracket to the vehicle but permit relative sliding movement between the first bracket and the vehicle when the first force of a predetermined magnitude is applied, wherein the decoupler assembly comprises a collar having a flange extending therefrom at one end, with teeth formed on a surface of the flange.

2. The mounting structure as claimed in claim 1 wherein the fastener is sized to be able to move along the length of the slot.

3. The mounting structure as claimed in claim 1 wherein the fastener is a bolt, stud or pin.

4. The mounting structure as claimed in claim 1 wherein the fastener also extends through a washer positioned adjacent to the flange of the collar so that when the fastener is used to fasten the first bracket to the vehicle the flange of the collar is urged into contact with the washer.

5. The mounting structure as claimed in claim 4 wherein the washer comprises two substantially parallel sidewalls arranged to capture the flange of the collar in order to retain the collar relative to the washer.

6. The mounting structure as claimed in claim 1 wherein a second bracket is provided, the second bracket being arranged to be mounted to the vehicle so that it is fixed relative to the vehicle, and a stop arranged to limit relative movement between the first bracket and the second bracket in one or more directions.

7. The mounting structure as claimed in claim 6 wherein the support for the seat belt is mounted to the first bracket and the stop of the second bracket is arranged to limit movement of the support for the seat belt.

8. The mounting structure as claimed in claim 7 wherein the support for the seat belt is a loop.

9. The mounting structure as claimed in claim 1 wherein a seat belt presenter mechanism is mounted to the bracket.

10. The mounting structure as claimed in claim 1 wherein more than one slot is formed in the bracket, and a respective decoupler assembly and fastener is associated with each elongate slot.

11. A mounting structure for mounting a support for a seat belt to a vehicle, the mounting structure being arranged so that when mounted to the vehicle the mounting structure will move relative to the vehicle in a first range of directions under application of a first force urging the mounting structure in one of the range of directions, but will not move relative to the vehicle in a direction outside the first range of directions when a second, greater, force is applied urging the mounting structure in such a direction, the mounting structure comprising a first bracket with an elongate slot extending therethrough, a decoupler assembly and a fastener extending through the decoupler assembly and the elongate slot, the fastener and decoupler assembly intended, in use, to fasten the first bracket to the vehicle but permit relative sliding movement between the first bracket and the vehicle when the first force of a predetermined magnitude is applied, wherein the decoupler assembly comprises a collar having a flange extending therefrom at one end, the fastener also extends through a washer positioned adjacent to the flange of the collar so that when the fastener is used to fasten the first bracket to the vehicle the flange of the collar is urged into contact with the washer, and wherein the washer defines an open ended slot.

12. A vehicle comprising a mounting structure for mounting a support for a seat belt to the vehicle, the mounting structure being mounted to the vehicle so that the mounting structure will move relative to the vehicle in a first range of directions under application of a first force urging the mounting structure in one of the range of directions, but will not move relative to the vehicle in a direction outside the first range of directions when a second, greater, force is applied urging the mounting structure in such a direction, the mounting structure comprising a bracket with an elongate slot extending therethrough, a decoupler assembly and a fastener extending through the decoupler assembly and the elongate slot, the fastener and decoupler assembly fastening the bracket to the vehicle but permitting relative sliding movement between the bracket and the vehicle when the first force of a predetermined magnitude is applied wherein the decoupler assembly comprises a collar having a flange extending therefrom at one end, with teeth formed on a surface of the flange.

13. The vehicle as claimed in claim 12, the vehicle being a motor car and the mounting structure being mounted to a rear quarter panel of the motor car in order to support an upper mounting point of the seat belt, wherein the seat belt is a three point seat belt for a front seat occupant of the motor car.

* * * * *